US006318890B1

(12) United States Patent
Hütter et al.

(10) Patent No.: US 6,318,890 B1
(45) Date of Patent: Nov. 20, 2001

(54) SINGLE CELL CALORIMETER

(75) Inventors: Thomas Hütter, Niederrohrdorf; Urs Jörimann, Bertschikon, both of (CH)

(73) Assignee: Mettler-Toledo GmbH, Greifensee (CH)

( * ) Notice: Subject to any disclaimer, the term of this patent is extended or adjusted under 35 U.S.C. 154(b) by 0 days.

(21) Appl. No.: 09/406,297

(22) Filed: Sep. 24, 1999

(30) Foreign Application Priority Data

Oct. 1, 1998 (EP) .................................................. 98118562

(51) Int. Cl.$^7$ .................................................. G01N 25/00
(52) U.S. Cl. .................................. 374/10; 374/11; 374/1; 374/43
(58) Field of Search .................................. 374/10, 11, 12, 374/13, 30, 29, 31, 33, 43, 39, 124, 1

(56) References Cited

U.S. PATENT DOCUMENTS

| | | | |
|---|---|---|---|
| 4,111,717 | * | 9/1978 | Baxter .................................... 136/225 |
| 4,178,800 | | 12/1979 | Thomann . |
| 5,033,866 | * | 7/1991 | Kehl et al. ............................ 374/179 |
| 5,059,543 | * | 10/1991 | Wise et al. ................................ 437/3 |
| 5,335,993 | * | 8/1994 | Marcus et al. ......................... 374/11 |
| 5,346,306 | * | 9/1994 | Readings et al. ....................... 374/10 |
| 5,484,204 | * | 1/1996 | Damley .................................. 374/10 |
| 5,599,104 | * | 2/1997 | Nakamura et al. ..................... 374/12 |
| 5,624,187 | * | 4/1997 | Reading .................................. 374/11 |
| 5,711,604 | * | 1/1998 | Nakamura ............................... 374/44 |
| 5,788,373 | * | 8/1998 | Huetter et al. ......................... 374/10 |
| 6,146,012 | * | 11/2000 | Nakamura et al. ..................... 374/10 |
| 6,192,697 | * | 2/2001 | Sahm et al. ............................. 62/223 |

FOREIGN PATENT DOCUMENTS

| | | |
|---|---|---|
| 9406000 | 3/1994 | (WO) . |
| 9533200 | 12/1995 | (WO) . |

OTHER PUBLICATIONS

Riou O et al:"A Very Sensitive Microcalorimetry Technique for Measuring Specific Heat of Mug Single . . . ", vol. 68, Mar. 1997, pp. 1501 –1509.

E. Lebsanft: A High–Sensitivity heat Flow Calorimeter for the Investigation of Metal–Hydrogen Reactions, vol. 12, No. 8, Aug. 1979, pp. 699–705.

P. Schrey E.A: "Measurement of Stored Energy of KBr After X–Irradiation at Low Temperature", vol. 10, No. 14, Jul. 1977, pp. 2511 –2521.

Point R. E.A.: "Reconstruction of Thermokinetics from Calorimert Data by Means of Numerical . . . ", vol. 17, No. 2, Dec. 1979, pp. 383–393.

* cited by examiner

*Primary Examiner*—Andrew H. Hirshfeld
*Assistant Examiner*—Gail Verbitsky
(74) *Attorney, Agent, or Firm*—Friedrich Kueffner

(57) ABSTRACT

A heat flow calorimeter comprises a single sample holder (5) in thermal contact with a heat source (1). A temperature difference over mutually spaced locations (11, 12) along a heat flow path between sample (23) and heat source (1) is measured. The measured signal (24, 25) is combined with a compensation signal from a signal source (34) to derive a compensated temperature difference signal representative of the net heat flow to sample (23), (FIG. 1).

11 Claims, 3 Drawing Sheets

SINGLE CELL CALORIMETER

The present invention relates to a single cell calorimeter comprising a heat source, a sample holder having a sample position thermally coupled to said heat source to thereby establish a heat flow path for a flow of heat between said heat source and a sample in said sample position, and a controller for controlling the amount of heating by said heat source.

Calorimeters may be used for the thermal analysis of various kinds of materials. A sample of the material placed in the sample position is heated by the heat source and the flow of heat between the heat source and the sample is evaluated to thereby derive structural and compositional information about the material, in particular heat capacity, phase transitions, onset temperatures, etc. Conventionally, for the sake of accuracy and dynamic range differential methods, for instance differential scanning calorimetry (DSC), are being used. In these differential methods, a reference position is arranged in the heat flow calorimeter symmetrically with respect to the sample position and a temperature difference is measured between a sample at the sample position and a known reference material at the reference position. The need for the reference position in addition to the sample position undesirably increases the expenditure of construction. More-over, any symmetry deviation in heat conduction between the heat source on the one hand and the sample and reference positions, respectively, on the other hand is detrimental for the accuracy of measurement.

A calorimeter of the type having separate sample and reference positions to perform a differential measurement between a sample in the sample position and a reference material in the reference position is described in EP 0 559 362 A1. In this known calorimeter, the controller controls a temperature of the heat source in accordance with a predetermined temperature program so as to cause said heat source temperature to vary in correspondence with a linear rise of temperature superposed by a periodic temperature modulation. A deconvolution technique is used to evaluate the measured differential signal to thereby derive from said measured differential signal two separate signal components caused by the linearly changing component and the modulation component of the heat source temperature, respectively.

WO 95/33199 and WO 95/33200 similarly disclose calorimeters designed for differential measurement between a sample in a sample position and a reference material in a reference position. In both cases, a temperature of the heat source is driven through a predetermined temperature program, said temperature program comprising two linearly changing parts of the same time duration in the first case and a linearly changing part superposed by a periodically changing part in the second case. The measured differential signal and a phase difference between the measured differential signal and the programmed temperature of the heat source are evaluated to separately derive a real and an imaginary signal portion.

It is an object of the present invention to provide for a heat flow calorimeter of the single-cell type having a simplified construction with small response time, less power requirement, smaller temperature grading, and smaller dimension. It is a further object to remove difficulties caused by symmetry deviations in heat flow to the sample position and a reference position.

In order to attain these objects, the single cell calorimeter according to the present invention is characterized by means for measuring a temperature difference between at least two locations spaced at a distance along said heat flow path to thereby provide a signal representative of said temperature difference, signal source means for providing a compensation signal representative of a flow of heat along said heat flow path when a sample is not located at said sample position, and means for evaluating said flow of heat between said sample in said sample position and said heat source on the basis of said measured temperature difference signal and said compensation signal.

According to the present invention, by measuring the temperature difference along the heat flow path to the sample position, there is no need for a reference position in the heat flow calorimeter with a resultant remarkable simplification and size reduction of the overall construction. The compensation signal from the signal source means takes account for any portion of the heat flow along the heat flow path which is not caused by the presence of the sample in the sample position. This enables the evaluating means to obtain the net amount of heat flow into or out of the sample.

The terms "heating", "heat flow", "heat source" and related terms are to be understood in the context of the present specification to mean either heating or cooling. In the latter case, the "heat source" will for instance be a source of cooling agent thermally coupled to the sample position.

The compensation signal may be predetermined for each individual setting and construction of the heat flow calorimeter, in particular the type of a crucible used to accommodate the sample and/or the type of atmosphere used in the calorimeter. With these experimental settings being fixed, the compensation signal will still depend on temperature conditions in the calorimeter. For this purpose, in a preferred embodiment of the heat flow calorimeter, means for measuring a heating temperature of said heat source to thereby provide a signal representative of said measured heating temperature is provided, said signal source means being operative to generate said compensation signal in accordance with a function of said measured heating temperature signal. This function may for instance be predetermined on the basis of a mathematical model using the laws of thermodynamics and/or empirical data, in particular polynomial functions fitting such empirical data to a desired degree of accuracy.

Preferably, the invention may be realized in that said compensation signal provided by said signal source means is representative of a temperature difference between said at least two mutually spaced locations along said heat flow path when a sample is not located in said sample position. When embodying the signal source means in this manner, the net heat flow to the sample is proportional to the difference between the measured temperature difference signal and the compensation signal with the proportionality factor being the heat resistance along the heat flow path which may be determined by conventional calibration methods. In such an embodiment, the evaluating means therefore comprises means for deriving a difference between said measured temperature difference signal and said temperature difference signal from said signal source means.

Like in conventional calorimetry, it is desirable to drive the sample through heating programs varying temperature as a function of time. These temperature variations may be linear heating or cooling scans as is the case in conventional DSC. Further, such linear scans may have superimposed any modulation function in accordance with known modulation techniques. To incorporate these techniques in the heat flow calorimeter according to the present invention, the controller comprises a programmer for controlling the amount of heating by said heat source in accordance with a desired temperature value as a function of time.

The temperature value resulting from the control of the heat source by the controller may be selected to be a temperature value of the heat source itself. This may be attained by establishing a direct control loop between a temperature sensor in the heat source and an actual value input terminal of the controller while the desired temperature value is applied by the programmer to a set value input terminal of the controller.

Alternatively, in accordance with another preferred embodiment of the present invention, the desired temperature value as a function of time is a temperature at said sample position when a sample is not located at said sample position, said controller comprising transformation means for transforming said desired temperature value into a corresponding temperature value of said heat source.

In this embodiment, again a direct control loop may be established between a measured temperature value of said heat source and an actual value input terminal of the controller. Further, the desired temperature value outputted from the programmer and corresponding to a temperature at the sample position when a sample is not located at the sample position is transformed in the transformation means and the transformed value is applied to the set value input of the controller.

Having regard to the sensing of the temperature difference along the heat flow path between the sample and the heat source, the present invention may be embodied in that said means for measuring said temperature difference is formed by a thermocouple having at least two thermosensitive junctions positioned along said heat flow path, one of said junctions being closer to said sample position than the other one. The electrical output signal of the thermocouple represents the temperature difference along the heat flow path. This signal is combined with the compensation signal from the signal source means, and the combined signal is proportional to the net heat flow between the sample and the heat source and is available for further analysis. In particular, the combined signal may be analyzed to derive the heat capacity of the sample as a function of temperature as known in the art, or may be deconvoluted in any other known way to derive one or more other signal portions which may be useful to characterize the sample material.

Preferably, said thermocouple comprises two sets of alternatingly series connected thermosensitive junctions arranged on two concentric circles centered around said sample position. The thermocouple thereby forms the sum of the thermovoltages caused by the temperature differences occurring in each pair of radially spaced thermosensitive junctions having the one junction of the pair located on the radially inner circle while the other junction of the pair is located on the radially outer circle. A crucible for accommodating the sample is preferably dimensioned so as to overlay the set of thermosensitive junctions on the radially inner circle while leaving the thermosensitive junctions on the radially outer circle uncovered.

In the following description the heat flow calorimeter in accordance with the invention is exemplarily explained with reference to the accompanying drawings, in which.

Figure 1:
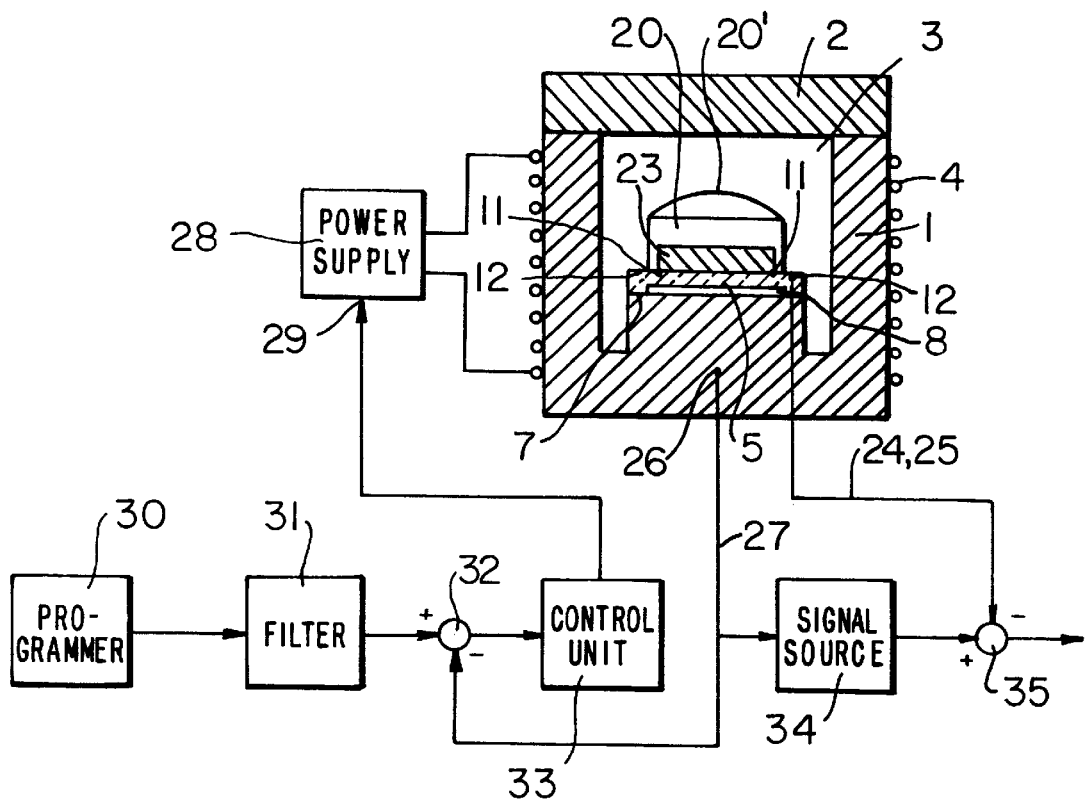
FIG. 1 is a schematic diagram of an embodiment of the heat flow calorimeter in accordance with the invention.

FIG. 1 schematically illustrates an essentially hollow cylindrical oven block 1 made of silver having the upper face thereof formed as a removable lid 2 for opening and closing block 1 to permit access to the interior 3 thereof. A winding of heating wire 4 is wound onto the exterior cylindrical surface of oven block 1 to provide for resistive heating. Alternatively, a flat resistive heater could be applied to the lower face of oven block 1 opposite to lid 2 or any other suitable portion of oven block 1.

A sample holder 5 is arranged in the interior 3 in thermal contact with oven block 1. As can be seen in more detail with further reference to FIGS. 2 and 3, sample holder 5 comprises a disk-shaped substrate 6 having the bottom side thereof in thermal contact with oven block 1. The area of contact 7 between oven block 1 and substrate 6 is defined by the outer circumference of substrate 6 and a circular recess 8 formed in the bottom side of substrate 6.

The upper side of substrate 6 has two layers 9, 10 of thermocouple ink printed thereon in a pattern so as to form a thermocouple composed of a plurality of series connected thermosensitive junctions 11, 12. As can best be seen from FIG. 2, the thermosensitive junctions 11, 12 are formed between overlapping portions of the lower and upper layers 9, 10 of thermocouple ink. This produces two sets of thermosensitive junctions 11, 12 located on two concentric circles of different radius. The thermosensitive junctions 11 and 12 of the two circles are circumferentially spaced under the same angular distance but mutually staggered at half of this angular distance. Each thermosensitive junction 11 on the inner circle is connected with two thermosensitive junctions 12 on the outer circle by a strip 13 of thermocouple ink of the lower layer 9 and a strip 14 of the upper layer, respectively, the circumferential offset between these connected junctions being one half of the angular distance between the thermosensitive junctions of each circle.

Two circumferentially adjacent strips 13 and 14 of thermocouple ink of the lower and upper layers 9, 10, respectively, have one end thereof connected to each of a connection pad 15, 16, respectively, formed on the upper face of the sample holder 5. Connection pads 15, 16 are located diametrically opposite and a semicircular conductor strip 17 extending radially outward the outer circle of thermosensitive junctions 12 is used to establish the connection between the end of strip 14 of thermocouple ink and connection pad 16.

Figure 2:
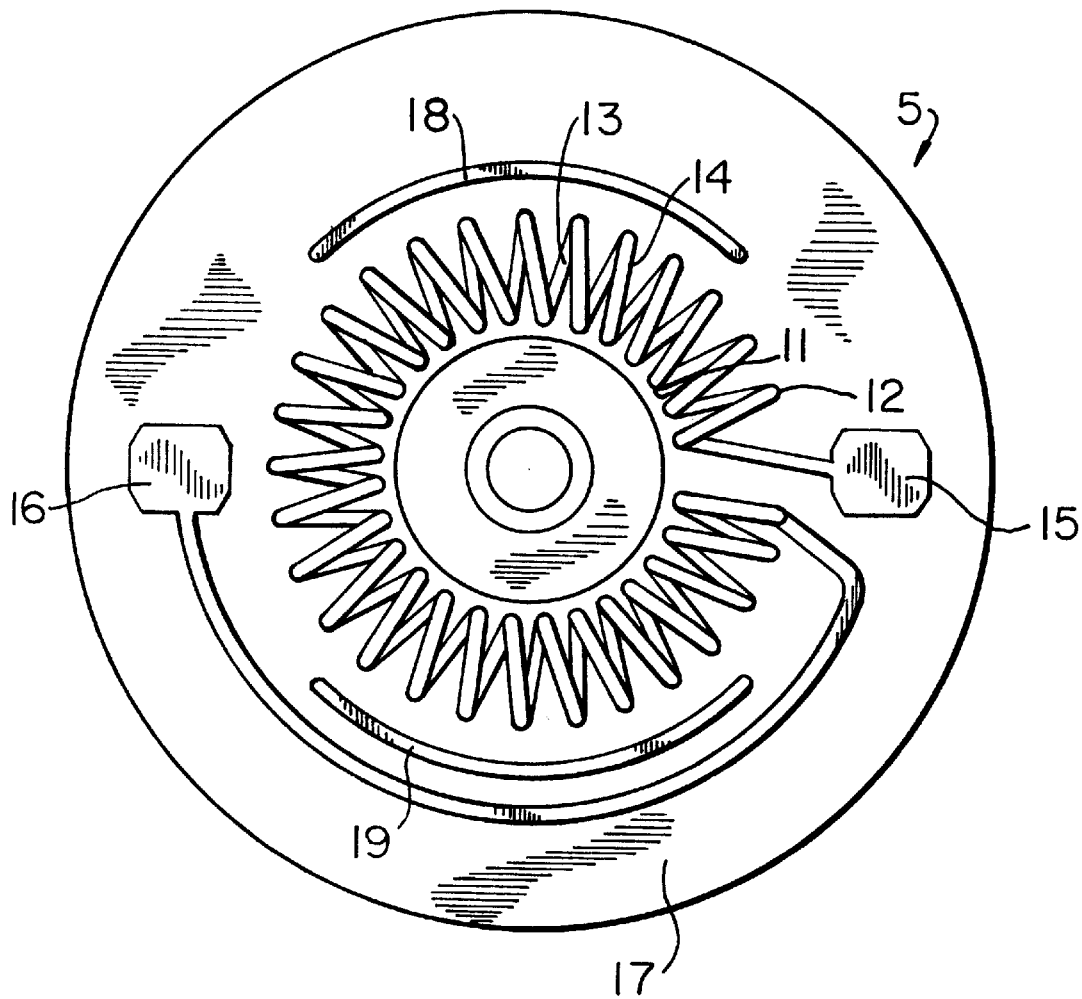
FIG. 2 illustrates a plan view of a sample holder for use in the heat flow calorimeter of FIG. 1.
Figure 3:
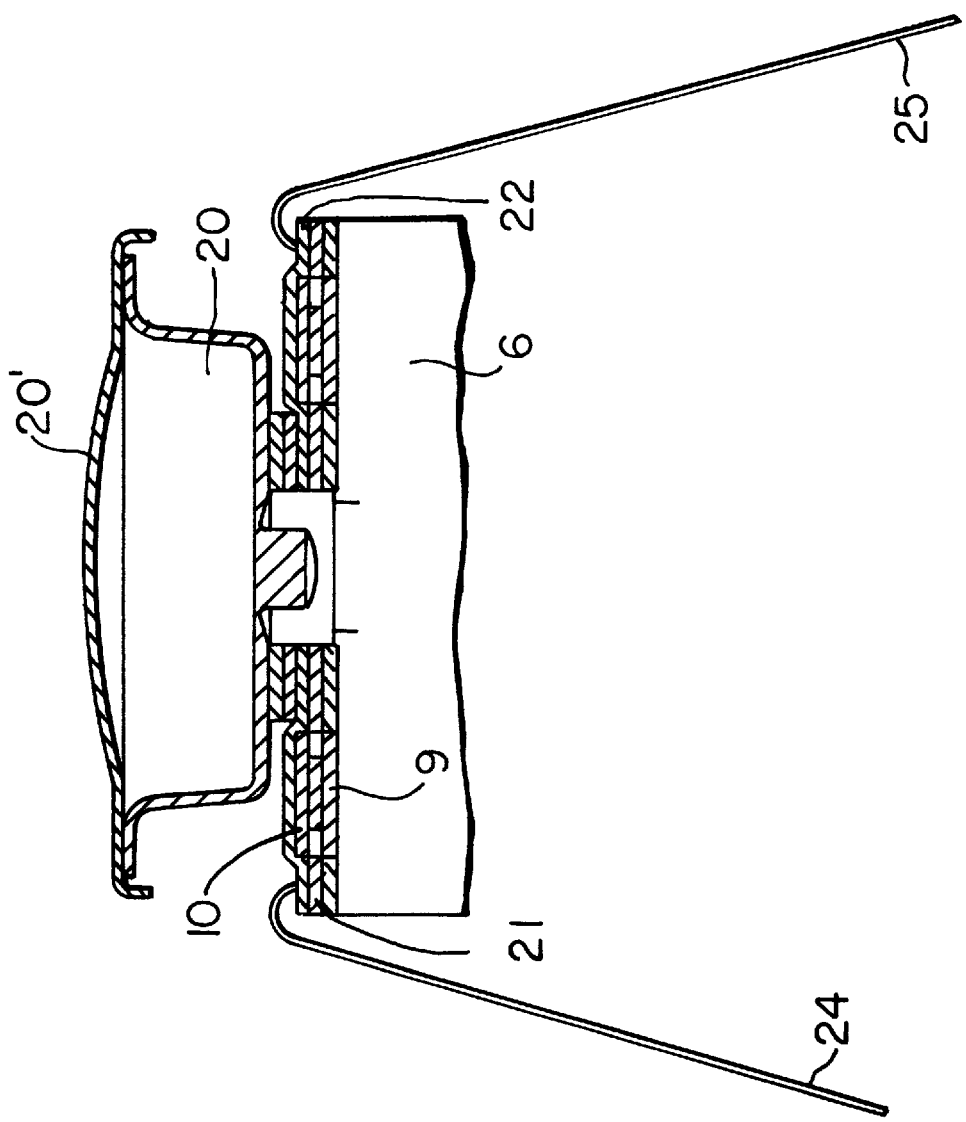
FIG. 3 shows a sectional view of the sample holder along the line III—III in FIG. 2 with a crucible located in the sample position.

FIG. 2 further shows two diametrically opposite strips 18, 19 in the form of portions of a circle concentrically arranged with the inner and outer circular loci of thermosensitive junctions 11, 12 and radially outside the locus of thermosensitive junctions 12 but inside the radius of semicircular conductor strip 17. These two strips 18, 19 act as positional aids to concentrically position a crucible 20 illustrated in FIG. 3.

The pattern of strips 13, 14 of thermocouple ink, connection pads 15, 16, conductor strip 17 and strips 18 and 19 is embedded into a dielectric material 21 providing for electric insulation and is covered by a protective overglaze 22.

By applying electric power to the heating wire 4, oven block 1 is heated to thereby act as a heat source causing a flow of heat to occur between oven block 1 and a sample 23 of material accommodated in crucible 20 having a removable lid 20'. Similarly, there is a heat flow between sample 23 and oven 1 in the alternative case of cooling where oven 1 is coupled to a source of cooling agent (not shown). In both cases, the flow path of heat extends across the radial outer circle of thermosensitive junctions 12 and the inner circle of thermosensitive junctions 11. This flow of heat causes a temperature difference to occur between the radially outer and inner thermosensitive junctions 12 and 11, respectively, and the thermocouple formed of the series connection of these thermosensitive junctions 11 and 12 generates an electrical output signal in proportion to said temperature difference. Signal wires 24, 25 are connected to connection pads 15 and 16, respectively, in order to receive the electrical temperature difference signal generated by the thermocouples.

Centrally located in the bottom portion of oven block 1 is a platinum thermometer 26 generating an output signal on signal line 27 which is representative of the temperature of oven block 1.

The heating power input to heating wire 4 is supplied by a controlled power supply 28. A controller coupled to a control input terminal 29 of said controlled power supply 28 comprises a programmer 30, a filter 31, an adder 32 and a control unit 33.

Programmer 30 is programmable to output a set value for the temperature of sample holder 5 having the empty crucible 20 located in the sample position, i.e. having crucible 20 in the sample position with no sample accommodated therein. This set value may be programmed to be a function of time. In particular, this function may include a linear ramp rising from a predetermined isothermal starting temperature at a starting time of the program until a predetermined end value of the temperature is reached at the time when the linear rise of the ramp is terminated. This is well-known from conventional DSC methods. Alternatively, the program for the set value may include a plurality of cycles of periodic temperature fluctuations between the starting and terminal points of time of the temperature program. In particular, the cyclic modulation may be combined with the linear ramp.

The set value outputted from programmer 30 is received by filter 31 and is transformed therein into a corresponding heating temperature of oven block 1. The transformation in filter 31 is so as to correspond to the temperature difference between the actual temperature at the sample position of the sample holder 5 when the empty crucible 20 is placed in the sample position and the heating temperature of oven block 1 is measured by thermometer 26, this temperature difference being due to the thermal resistance between the sample position including the empty crucible and the oven. The filter constants for filter 31 necessary to provide for this transformation may be obtained by conventional calibration methods. The transformed temperature set value outputted from filter 31 is applied to the non-inverting input of adder 32 while the heating temperature measured by thermometer 26 is applied to the inverting input terminal thereof. The difference signal outputted from adder 32 is applied to the control input terminal of control unit 33 thereby causing control unit 33 to apply a corresponding control signal to the control input terminal 29 of power supply 28. As a consequence, the heating power applied to heating wire 4 is controlled so as to yield a temperature value at the empty sample position in compliance with the set value provided as the output of programmer 30.

Reference numeral 34 designates a signal source designed to output a compensation signal which corresponds to the output signal of the thermocouple at sample holder 5 for the case that the sample is not located in crucible 20, i.e. only the empty crucible 20 is placed in the sample position. The compensation signal from signal source 34 is applied to the inverting input terminal of an adder 35 having the temperature difference signal on signal wires 24, 25 applied to the inverting input terminal thereof. As a result, adder 35 outputs a compensated temperature difference signal which is representative of the net heat flow caused by the presence of sample 23. Adder 35 may be part of a larger evaluation means which operates to further analyze the compensated temperature difference signal in order to derive characteristic parameters of the sample, for instance the sample specific heat capacity as a function of sample temperature. Such analysis techniques are well known in the art.

Signal source 34 may implement any suitable calculational model for the temperature difference signal in the absence of the sample 23. Assuming a linear system response to changes of the heating temperature To as measured by platinum thermometer 26, the compensation signal $\Delta T$ may be described in terms of a linear differential equation as $$\Delta T + \tau \frac{d(\Delta T)}{dt} = (\Delta T)_{iso} - k\frac{dT_0}{dt} \quad (1)$$

where $\tau$ is a response time constant and k another parameter of the system and $(\Delta T)_{iso}$ is an isothermal offset.

For a given configuration, the parameters $\tau$, k and $(\Delta T)$iso are functions of the heating temperature $T_0$. Explicit expressions for $\tau$ and $(\Delta T)$iso as functions of To may be obtained through well known system identification techniques, e.g. in terms of polynomial fits.

In heating programs used in general, often the effects of transient do not play a role. In this case, the second term on the left-hand side of equation (1) is zero. A mathematical expression for the compensation signal is then $$\Delta T = (\Delta T)_{iso} - k\frac{dT_0}{dt} \quad (2)$$

This mathematical expression is stored in signal source 34 and the heating temperature To on signal line 27 is applied to the input of signal source 34 thereby enabling signal source 34 to calculate the value of the compensation signal $\Delta T$ for each applied input value of the heating temperature $T_0$.

What is claimed is:

1. A single cell calorimeter comprising:
   a heat source;
   a sample holder having a sample position thermally coupled to said heat source to thereby establish a heat flow path for a flow of heat between said heat source and a sample in said sample position;
   a controller for controlling the amount of heating by said heat source;
   means for measuring a first temperature difference between at least two locations spaced at a distance along said heat flow path to thereby provide a measured temperature difference signal;
   signal source means for providing a compensation signal representative of a flow of heat along said heat flow path when a sample is not located at said sample position; and
   means for evaluating said flow of heat between said sample in said sample position and said heat source on the basis of said measured temperature difference signal and said compensation signal.

2. A calorimeter according to claim 1, wherein means for measuring a heating temperature of said heat source to thereby provide a signal representative of said measured heating temperature is provided, said signal source means being operative to generate said compensation signal in accordance with a function of said measured heating temperature signal.

3. A calorimeter according to claim 1, wherein said compensation signal provided by said signal source means is representative of a second temperature difference between said at least two mutually spaced locations along said heat flow path when a sample is not located in said sample position.

4. A calorimeter according to claim 3, wherein said evaluating means comprises means for deriving a difference between said measured temperature difference signal and said compensation signal from said signal source means.

5. A calorimeter according to claim 1, wherein said controller comprises a programmer for controlling the amount of heating by said heat source in accordance with a desired temperature value as a function of time.

6. A calorimeter according to claim 5, wherein said desired temperature value as a function of time includes an essentially linear component superimposed by any modulation function.

7. A calorimeter according to claim 5, wherein said desired temperature value as a function of time is a temperature at said sample position when a sample is not located at said sample position, said controller comprising transformation means for transforming said desired temperature value into a corresponding temperature value of said heat source.

8. A calorimeter according to claim 1, wherein said means for measuring said first temperature difference is formed by a thermocouple having at least two thermosensitive junctions positioned along said heat flow path, one of said junctions being closer to said sample position than the other one.

9. A calorimeter according to claim 8, wherein said thermocouple comprises two sets of alternatingly series connected thermosensitive junctions arranged on two concentric circles centered around said sample position.

10. A calorimeter according to claim 1, wherein said sample position is adapted to receive a crucible in thermal contact, said crucible being formed to receive said sample therein.

11. A calorimeter according to claim 1, wherein said signal source means comprises means for storing a mathematical expression defining said compensation signal as a function of the heating temperature of said heat source, and means for evaluating said expression in response to the input of the heating temperature value to thereby provide said compensation signal.

* * * * *